(12) United States Patent
Buchter

(10) Patent No.: US 9,645,088 B2
(45) Date of Patent: May 9, 2017

(54) DEVICE FOR ANALYZING THE MATERIAL COMPOSITION OF AN OBJECT VIA PLASMA SPECTRUM ANALYSIS

(71) Applicant: Rigaku Americas Holding, Inc., The Woodlands, TX (US)

(72) Inventor: Scott Charles Buchter, Espoo (FI)

(73) Assignee: RIGAKU AMERICAS HOLDING, INC., The Woodlands, TX (US)

( * ) Notice: Subject to any disclaimer, the term of this patent is extended or adjusted under 35 U.S.C. 154(b) by 0 days.

(21) Appl. No.: 14/870,419

(22) Filed: Sep. 30, 2015

(65) Prior Publication Data

US 2017/0089839 A1    Mar. 30, 2017

(51) Int. Cl.
*G01J 3/30* (2006.01)
*G01N 21/71* (2006.01)

(52) U.S. Cl.
CPC ..... *G01N 21/718* (2013.01); *G01N 2201/0612* (2013.01); *G01N 2201/0636* (2013.01); *G01N 2201/0697* (2013.01)

(58) Field of Classification Search
CPC .... G01N 21/71; G01N 21/718; G01N 21/645; G01N 21/6458; G01J 3/02; G01J 3/4406
See application file for complete search history.

(56) References Cited

U.S. PATENT DOCUMENTS

| 6,700,094 B1 * | 3/2004 | Kuntze | B41J 3/36 219/121.6 |
| 6,982,796 B2 * | 1/2006 | Sato | G01J 3/18 356/503 |

\* cited by examiner

*Primary Examiner* — Abdullahi Nur
(74) *Attorney, Agent, or Firm* — Brinks Gilson & Lione

(57) ABSTRACT

A device for analyzing the material composition of an object via plasma spectrum analysis includes an optical assembly having a first aspheric mirror and a second aspheric mirror. The first and second aspheric mirrors have an aspheric surface profile. The first aspheric mirror is configured to receive a laser beam at non-normal incidence along a first axis. The optical assembly is configured such that the first aspheric mirror directs the beam to the object for plasma spectrum analysis along a second axis, the second axis being different from the first axis. The plasma emitted light emitted is collected coaxially along the second axis and redirected along the first axis in the opposite direction by the first aspheric mirror. The second aspheric mirror is configured to redirect a portion of the plasma emitted light along a third axis to a spectrometer for analysis.

17 Claims, 3 Drawing Sheets

DEVICE FOR ANALYZING THE MATERIAL COMPOSITION OF AN OBJECT VIA PLASMA SPECTRUM ANALYSIS

BACKGROUND

1. Field of the Invention

The present invention generally relates to laser-induced breakdown spectroscopy systems 2. Description of Related Art Laser-induced breakdown spectroscopy ("LIBS") is a type of atomic emission spectroscopy which uses a highly energetic laser pulse as the excitation source. The laser is focused to form a plasma, which atomizes and excites samples. In principle, LIBS can analyze any matter regardless of its physical state, be it solid, liquid, or gas. Because all elements emit light of characteristic frequencies when excited to sufficiently high temperatures, LIBS can detect all elements, limited only by the power of the laser beam utilized as well as the sensitivity and wavelength range of the spectrograph and detector.

If the constituents of a material to be analyzed are known, LIBS may be used to evaluate the relative abundance of each constituent element, or to monitor the presence of impurities. In practice, detection limits are a function of a) the plasma excitation temperature, b) the light collection window, and c) the line strength of the viewed transition. LIBS makes use of optical emission spectrometry and is to this extent very similar to arc/spark emission spectroscopy.

LIBS operate by focusing the laser beam onto a small area at the surface of the specimen When the laser beam is discharged it ablates a very small amount of material, in the range of nanograms to picograms, which generates a plasma plume with temperatures in excess of 100,000 K. During data collection, typically after local thermodynamic equilibrium is established, plasma temperatures range from 5,000-20,000 K. At the high temperatures during the early plasma, the ablated material dissociates (breaks down) into excited ionic and atomic species. During this time, the plasma emits a continuum of radiation which does not contain any useful information about the species present, but within a very small timeframe the plasma expands at supersonic velocities and cools. At this point the characteristic atomic emission lines of the elements can be observed.

SUMMARY

A system for analyzing the material composition of an object via plasma spectrum analysis includes an optical assembly having a first aspheric mirror and a second aspheric mirror. The first and second aspheric mirrors each have an aspheric surface profile. The first aspheric mirror is configured to receive a laser beam at non-normal incidence along a first axis. The optical assembly is configured such that the first aspheric mirror directs the beam to the object for plasma spectrum analysis along a second axis, which is different from the first axis. The plasma emitted light emitted is collected coaxially along the second axis and redirected along the first axis in the opposite direction by the first aspheric mirror. The second aspheric mirror is configured to redirect a portion of the plasma emitted light along a third axis to a spectrometer for analysis.

The axis of the laser beam from a laser assembly may be substantially perpendicular to the axis of the laser beam directed toward and striking the object. In addition, the beam path of the plasma emitted light between the object and the device may share the beam path of the laser beam striking the object.

In addition to the first and second aspheric mirrors, the optical assembly may further include a first mirror, a second mirror, and a dichroic mirror. The first mirror may be configured to receive the laser beam from the laser assembly, wherein the beam from the laser assembly is projected along a third axis. The second mirror may be configured to receive the laser beam from the first mirror. The second and third axis may be parallel to each other and may therefore be both perpendicular to the first axis.

The dichroic mirror may be configured to receive the laser beam from the second mirror. The first aspheric mirror may be configured to receive the beam from the dichroic mirror and direct the beam to the object along the second axis. The plasma light generated by the laser beam striking the object is received by the second aspheric mirror from the first aspheric mirror and is then direct to the plasma emitted light to the spectrometer for analysis. The dichroic mirror may be located substantially between the first aspheric mirror and the second aspheric mirror.

Further objects, features and advantages of this invention will become readily apparent to persons skilled in the art after a review of the following description, with reference to the drawings and claims that are appended to and form a part of this specification.

DETAILED DESCRIPTION

Figure 1:
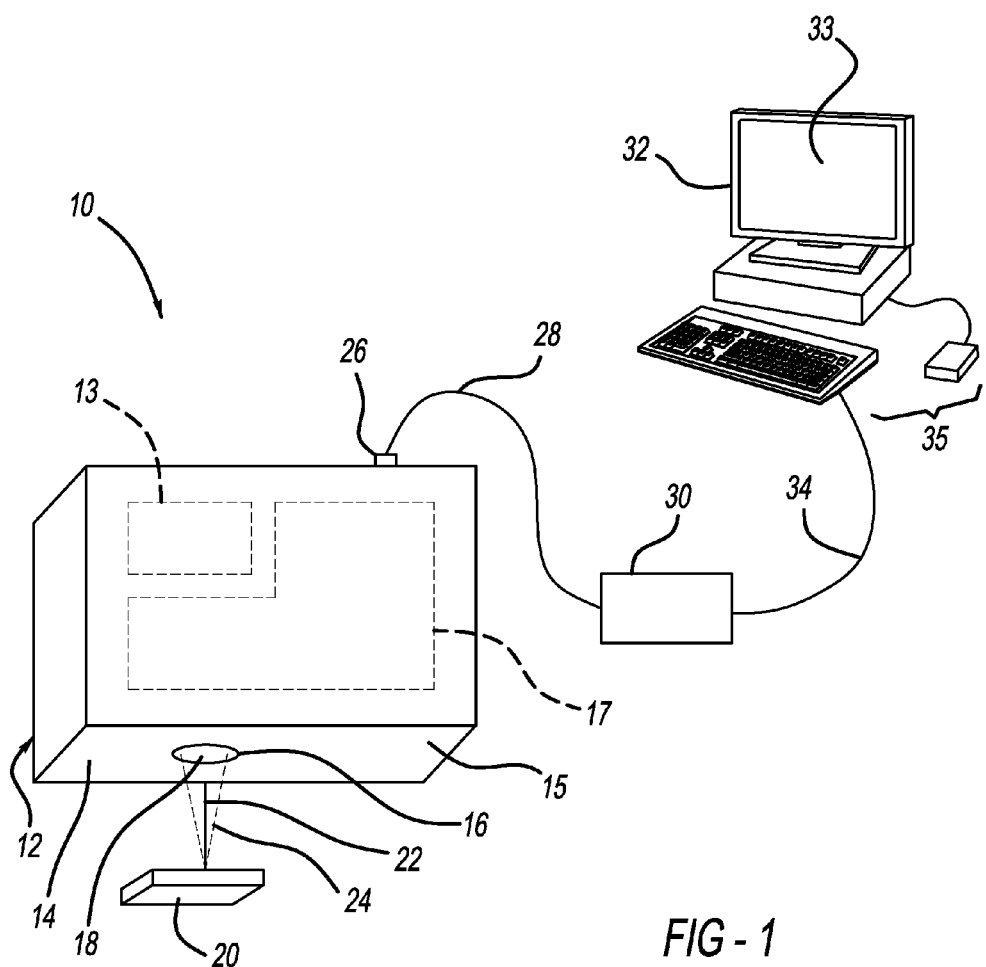
FIG. 1 illustrates a block diagram of a system for analyzing the material composition of an object via plasma spectrum analysis.

Referring to FIG. 1, a system 10 for analyzing the material composition of an object 20 by spectrum analysis is shown. As its primary components, the system 10 includes a device 12 for analyzing the material composition of the object 20. The device 12 may include a housing 14 which may enclose a number of components that will be described in FIG. 2 and later in this description. For example, the housing 14 may include a laser assembly 13 for producing a laser beam 22 and an optical assembly 17 for directing a laser beam 22 to the object 20. In addition, the optical assembly 17 may function to direct plasma emitted light 24 to a spectrometer 30 via an optical fiber 28.

The device 12 has two primary functions. The device 12 provides beam shaping and delivery for the laser beam 22 and also efficiently collects the plasma emitted light 24 from the plasma for delivery to the spectrometer 30. The laser beam 22 may be a single mode laser beam having a focused diameter of 20 microns on the object 20 in order to generate a strong plasma plume. The working distance may be around or greater than 10 mm.

A wall portion 15 of the housing 14 may have an opening 16 formed therein. The opening 16 may contain a window 18. The window 18 may be a transparent window allowing for the transmission of light to and from the device 12, such as the laser beam 22 and the plasma emitted light 24. The housing 14 may be hermetically sealed and may be filled with an inert gas.

As stated before, the device 12 is configured to emit a laser beam 22 towards the object 20. When the laser beam 22 strikes the object 20, a plasma plume is formed and plasma emitted light 24 is reflected back to the window 18. As will be described in more detail in FIG. 2, the plasma emitted light 24 is redirected to the spectrometer 30 via the optical fiber 28. The fiber adapter 26 optically directs the plasma emitted light 24 to the optical fiber 28. The optical fiber 28 in turn directs the plasma emitted light 24 to a spectrometer 30.

The spectrometer 30 may perform a number of different spectral analyses of the plasma emitted light 24 and converts these optical signals into electrical signals that are provided to digital analyzer 32.

The spectrometer 30 may include a monochromator (scanning) or a polychromator (non-scanning) and a photomultiplier or CCD (charge coupled device) detector, respectively. The spectrometer 30 collects electromagnetic radiation over the widest wavelength range possible, maximizing the number of emission lines detected for each particular element. The response of the spectrometer 30 may be from 1100 nm (near infrared) to 170 nm (deep ultraviolet).

The electrical signals generated by the spectrometer 30 may be provided to the digital analyzer 32 by a cable 34. However, it should be understood that any one of a number of different methodologies utilized to transmit digital data from separate devices may be employed. For example, the digital analyzer 32 may utilize a wireless protocol to communicate with the spectrometer 30. The digital analyzer 32 may be a dedicated device having an output device 33 and one or more input devices 35. The output device 33 may be a display, while the input device 35 may be a keyboard and/or a mouse.

Figure 2:
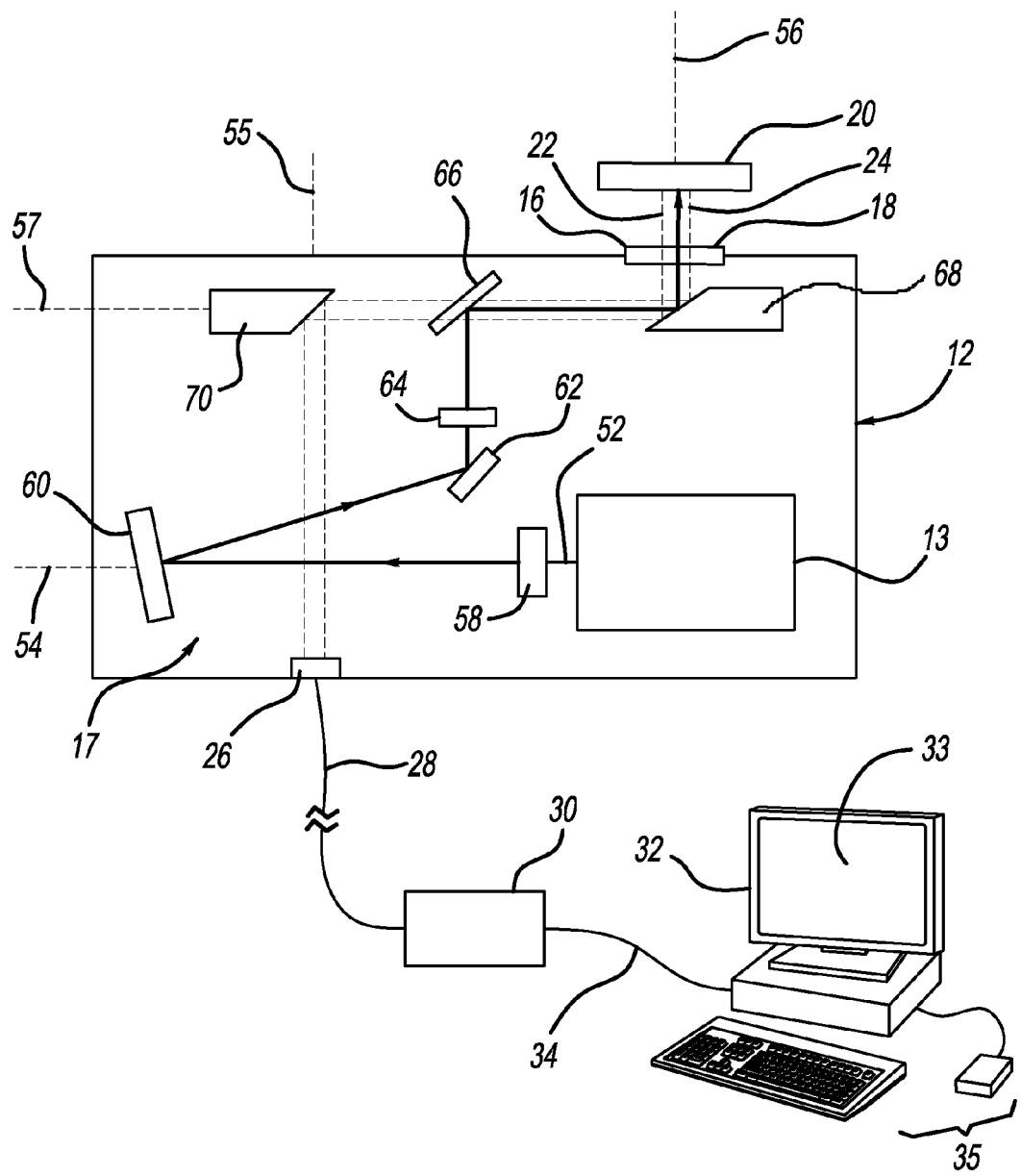
FIG. 2 illustrates a block diagram of the internal components of the system for analyzing the material composition of an object via plasma spectrum analysis of FIG. 1.

Referring to FIG. 2, the device 12 may also include a laser assembly 13 for generating a laser beam 22 and an optical assembly 17 for directing the laser beam 22 to the object 20. In addition, the optical assembly 17 may direct the plasma emitted light 24 towards the fiber coupler 26. The laser assembly 13 may be a Nd:YAG laser that may generate energy in the near infrared region of the electromagnetic spectrum, with a wavelength of 1064 nm. The pulse duration may be in the region of 10 ns.

The laser assembly 13 is configured to output a laser beam 52. The laser beam 52 is directed along an axis 54 towards a mirror 60. From there, the laser beam 52 is directed from the mirror 60 to a second mirror 62. The second mirror 62 directs the laser to a dichromic mirror 66.

The dichromic mirror 66 has the ability to reflect light at one wavelength, while allowing light at a different wavelength to pass though. Here, the dichromic mirror 66 may have a high reflectivity of the laser beam 52, which, as said previously, may be 1064 nm excitation light and high transmission for the plasma emitted light 24, which may be ultraviolet signal light. The dichromic mirror 66 allows both excitation laser beam 52 and signal collection to be coaxial.

The dichromic mirror 66 directs the laser beam 52 to a first aspheric mirror 68. The first aspheric mirror 68 directs the laser beam 52 (now laser beam 22) towards the object 20 along the axis 56. It is noted that the axis 54 and the axis 56 have different angles. The axis 54 and the axis 56 may have angles that are substantially perpendicular to one another. The laser beam 22 may be directed to the object 20 via the window 18. As the laser beam 22 strikes the object 20, a plasma is generated.

The plasma emitted light 24 is then directed back to the first aspheric mirror 68 along the axis 56. The first aspheric mirror 68 redirects the plasma emitted light 24 along another axis 57 towards the dichromic mirror 66. As stated before, the dichromic mirror 66 is reflective for certain wavelengths of light but is transmissive at other wavelengths. Here, the plasma emitted light 24 has such a wavelength that it will substantially pass through the dichromic mirror 66 to a second aspheric mirror 70.

The second aspheric mirror 70 will direct the light along an axis 55 towards a fiber coupler 26. The fiber coupler 26 receives and focuses the light to an optical fiber 28 which then provides this light to a spectral analyzer 30.

The optical assembly 17 may also include lenses 58 and 64. The lens 58 is generally located between the laser assembly 13 and the mirror 60. The lens 64 is generally located between the mirror 62 and the dichromic mirror 66. The lens 58 may have a positive or negative focal length, while the lens 64 will only have a positive focal length. The lenses 58 and 64 serve to the focus the laser beam 52 on the mirror 60 and the dichromic mirror 66, respectively.

Figure 3:
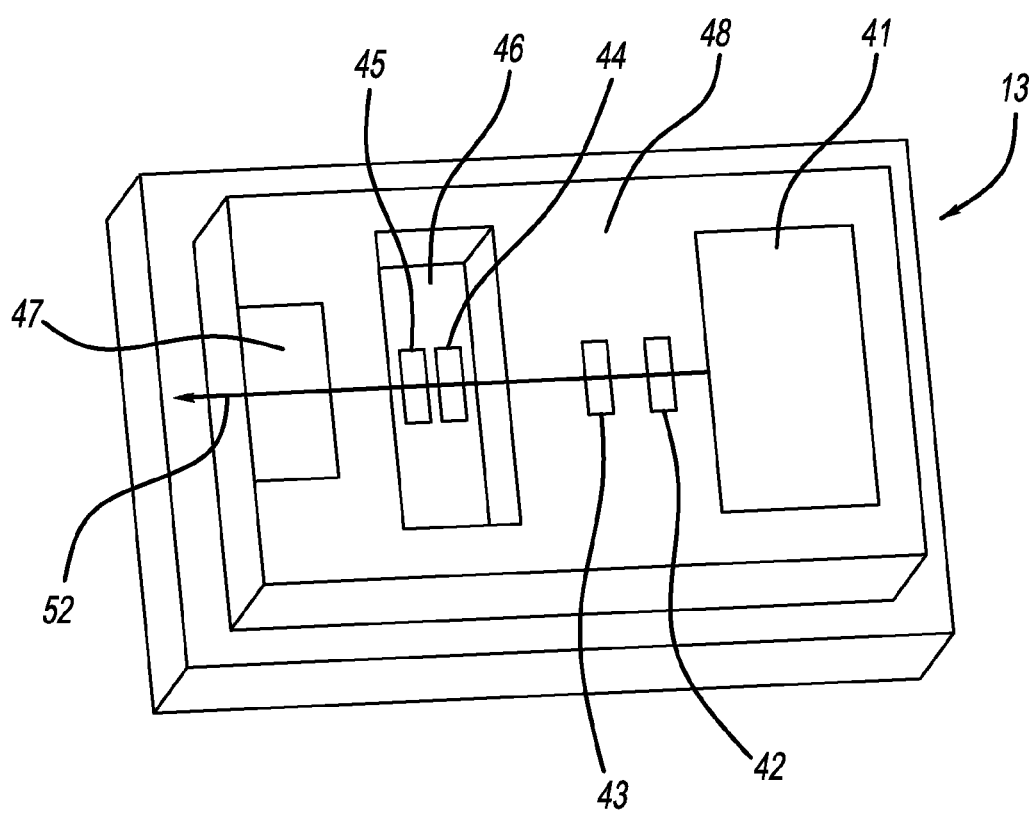
FIG. 3 illustrates a block diagram of a laser assembly for use with the system for analyzing the material composition of an object via plasma spectrum analysis.

Referring to FIG. 3, a more detailed view of the laser assembly 13 is shown. The laser assembly 13 may be a diode-pumped solid-state laser. A diode-pumped solid-state laser pumps a solid gain medium, for example, a ruby or a neodymium-doped YAG crystal, with a laser diode.

As such, the laser assembly 13 includes a pump diode 41. Light emitted by the pump diode 41 is focused by lenses 42 and 43 and to a laser crystal 44. A q-switch 45 is provided thereafter. From there, the beam is provided to an output mirror 47 where it is outputted to the lens 58 of FIG. 2. A resonator is essentially formed by the reflecting surfaces in which the laser crystal 44 and a Q-switch 45 are arranged. The Q-switch 45 may be a passive Q-switch. Q switching is a technique for obtaining energetic short pulses from a laser by modulating the intracavity losses and thus the Q factor of the laser resonator. The technique is mainly applied for the generation of nanosecond pulses of high energy and peak power with solid-state bulk lasers.

As a person skilled in the art will readily appreciate, the above description is meant as an illustration of implementation of the principles this invention. This description is not intended to limit the scope or application of this invention in that the invention is susceptible to modification, variation and change, without departing from the spirit of this invention, as defined in the following claims.

The invention claimed is:

1. A device for analyzing the material composition of an object via plasma spectrum analysis, the device comprising: an optical assembly having a first aspheric mirror with an aspheric surface profile configured to receive a laser beam at non-normal incidence along a first axis; the optical assembly being configured such that the aspheric mirror directs the beam to the object for plasma spectrum analysis along a second axis, the second axis being different from the first axis; wherein the plasma emitted light emitted from the plasma is collected coaxially along the second axis and redirected along the first axis in the opposite direction by the first aspheric mirror; and the optical assembly having a second aspheric mirror, the second aspheric mirror configured to redirect a portion of the plasma emitted light along a third axis, the second aspheric mirror having an aspheric surface profile: a housing, the housing substantially enclosing the optical assembly, a window located between the first aspheric mirror and the object, wherein the window is located within a wall of the housing; a fiber adaptor, the fiber adaptor being configured to receive the portion of the plasma emitted light along the third axis, the fiber adaptor is configured to optically direct the plasma emitted light to an optical fiber to a spectrometer for analysis, the second aspheric mirror having an aspheric surface profile.

2. The device of claim 1, wherein the first axis is substantially perpendicular to the second axis.

3. The device of claim 1, wherein the optical assembly further comprises:
   a first mirror configured to receive the beam from the laser assembly, the beam from the laser assembly being projected along the first axis;
   a second mirror, the first mirror being configured to direct the beam to the second mirror, the second mirror being configured to receive the beam from the first mirror;
   a dichroic mirror, the second mirror being configured to direct the beam to the dichroic mirror, the dichroic mirror configured to receive the beam from the second mirror;
   the first aspheric mirror configured to receive the beam from the dichroic mirror and direct the beam to the object along the second axis;
   the second aspheric mirror configured to receive the plasma emitted light from the first aspheric mirror and direct the plasma emitted light to a spectrometer; and
   the dichroic mirror being located substantially between the first aspheric mirror and the second aspheric mirror.

4. The device of claim 3, wherein the optical assembly further comprises:
   a first lens located between laser assembly and the first mirror, the first lens being configured to focus the beam from the laser assembly to first mirror, the first lens having a positive or negative focal length; and
   a second lens located between the second mirror and the dichroic mirror, the second lens being configured to focus the beam from the second mirror to the dichroic mirror, the second lens having a positive focal length.

5. The device of claim 1, wherein the device further comprises the laser assembly.

6. The device of claim 5, wherein the laser assembly is a q-switched laser assembly.

7. The device of claim 6, wherein the a q-switched laser assembly comprises:
   a laser crystal;
   focusing elements;
   a pump radiation source whose pump radiation is focused through the focusing elements in the laser crystal; and
   a resonator formed by reflecting surfaces in which at least one laser crystal, and a passive Q-switch are arranged.

8. The device of claim 1, wherein the device further comprises the laser assembly, the laser assembly being substantially enclosed within the housing.

9. The device of claim 8, wherein the laser assembly is a q-switched laser assembly.

10. The device of claim 9, wherein the a q-switched laser assembly comprises:
    a laser crystal;
    focusing elements;
    a pump radiation source whose pump radiation is focused through the focusing elements in the laser crystal; and
    a resonator formed by reflecting surfaces in which at least one laser crystal, and a passive Q-switch are arranged.

11. A device for analyzing the material composition of an object via plasma spectrum analysis, the device comprising:
    an optical assembly having a first aspheric mirror with an aspheric surface profile configured to receive a laser beam at non-normal incidence along a first axis;
    the optical assembly being configured such that the aspheric mirror directs the beam to the object for plasma spectrum analysis along a second axis, the second axis being different from the first axis;
    wherein the plasma emitted light emitted from the plasma is collected coaxially along the second axis and redirected along the first axis in the opposite direction by the first aspheric mirror; and
    the optical assembly having a second aspheric mirror, the second aspheric mirror configured to redirect a portion of the plasma emitted light along a third axis to a spectrometer for analysis, the second aspheric mirror having an aspheric surface profile;
    wherein the first axis is substantially perpendicular to the second axis;
    wherein the optical assembly further comprises:
       a first mirror configured to receive the beam from the laser assembly, the beam from the laser assembly being projected along the first axis;
       a second mirror, the first mirror being configured to direct the beam to the second mirror, the second mirror being configured to receive the beam from the first mirror;
       a dichroic mirror, the second mirror being configured to direct the beam to the dichroic mirror, the dichroic mirror configured to receive the beam from the second mirror;
       the first aspheric mirror configured to receive the beam from the dichroic mirror and direct the beam to the object along the second axis;
       the second aspheric mirror configured to receive the plasma emitted light from the first aspheric mirror and direct the plasma emitted light to a spectrometer; and
       the dichroic mirror being located substantially between the first aspheric mirror and the second aspheric mirror.

12. The device of claim 11, wherein the optical assembly further comprises:
    a first lens located between laser assembly and the first mirror, the first lens being configured to focus the beam from the laser assembly to first mirror, the first lens having a positive or negative focal length; and
    a second lens located between the second mirror and the dichroic mirror, the second lens being configured to focus the beam from the second mirror to the dichroic mirror, the second lens having a positive focal length.

13. The device of claim 12, further comprising a window located between the first aspheric mirror and the object.

14. The device of claim 13, further comprising a housing, the housing substantially enclosing the optical assembly.

15. The device of claim 14, wherein the window is located within a wall of the housing.

16. The device of claim 12, wherein the device further comprises the laser assembly.

17. The device of claim 16, wherein the laser assembly is a q-switched laser assembly.

* * * * *